(12) United States Patent
Garcia Molina et al.

(10) Patent No.: US 11,253,673 B2
(45) Date of Patent: Feb. 22, 2022

(54) DETERMINING CORRECTED TIMING OF STIMULATION PROVIDED TO A SUBJECT DURING SLEEP

(71) Applicant: KONINKLIJKE PHILIPS N.V., Eindhoven (NL)

(72) Inventors: Gary Nelson Garcia Molina, Madison, WI (US); Anandi Mahadevan, Murrysville, PA (US); Surya Subrahmanya Sreeram Vissapragada Venkata Satya, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 265 days.

(21) Appl. No.: 16/466,794

(22) PCT Filed: Dec. 7, 2017

(86) PCT No.: PCT/EP2017/081840
§ 371 (c)(1),
(2) Date: Jun. 5, 2019

(87) PCT Pub. No.: WO2018/104459
PCT Pub. Date: Jun. 14, 2018

(65) Prior Publication Data
US 2019/0336723 A1 Nov. 7, 2019

Related U.S. Application Data

(60) Provisional application No. 62/431,482, filed on Dec. 8, 2016.

(51) Int. Cl.
*A61M 21/02* (2006.01)
*A61B 5/00* (2006.01)
(Continued)

(52) U.S. Cl.
CPC ............ *A61M 21/02* (2013.01); *A61B 5/369* (2021.01); *A61B 5/4812* (2013.01);
(Continued)

(58) Field of Classification Search
CPC ...... A61M 2230/06; A61M 2021/0027; A61M 2230/50; A61M 2021/0072;
(Continued)

(56) References Cited

U.S. PATENT DOCUMENTS 3,893,450 A 7/1975 Ertl
6,067,467 A 5/2000 John
(Continued)

FOREIGN PATENT DOCUMENTS

| CN | 202105317 U | 1/2012 |
| WO | 2016092515 A1 | 6/2016 |
| WO | 2016166202 A1 | 10/2016 |

OTHER PUBLICATIONS

International Search Report and Written Opinion, International Application No. PCT/EP2017/081840, dated Apr. 13, 2018.
(Continued)

*Primary Examiner* — Christine H Matthews
*Assistant Examiner* — Joshua Daryl D Lannu

(57) ABSTRACT

The system receives a raw signal carrying information related to slow wave activity; buffers a portion of the raw signal; determines a timing of slow wave events in the buffered portion of the raw signal; filters the raw signal; determines a timing of slow wave events in the filtered raw signal; compares the timing of the slow wave events in the buffered portion of the raw signal to the timing of the slow wave events in the filtered raw signal; determines a first correction factor associated with reducing slow wave activity in the subject and a second correction factor associated with enhancing slow wave activity in the subject; and
(Continued)

adjusts a timing of the stimulation provided to the subject during the sleep session based on the first and/or second correction factors.

21 Claims, 8 Drawing Sheets

(51) Int. Cl.
*A61B 5/0476* (2006.01)
*A61B 5/369* (2021.01)
*A61M 21/00* (2006.01)

(52) U.S. Cl.
CPC ... *A61B 5/7203* (2013.01); *A61M 2021/0016* (2013.01); *A61M 2021/0022* (2013.01); *A61M 2021/0027* (2013.01); *A61M 2021/0044* (2013.01); *A61M 2021/0055* (2013.01); *A61M 2021/0072* (2013.01); *A61M 2205/50* (2013.01); *A61M 2230/10* (2013.01)

(58) Field of Classification Search
CPC ...... A61M 2230/42; A61M 2021/0044; A61M 2021/0055; A61M 2230/63; A61M 2205/50; A61M 21/02; A61M 2230/10; A61M 2021/0022; A61M 2021/0016; A61M 2205/332; A61M 2205/3368; A61B 5/369; A61B 5/7203; A61B 5/4836; A61B 5/4812
See application file for complete search history.

(56) References Cited

U.S. PATENT DOCUMENTS

| | | | |
|---|---|---|---|
| 2004/0097802 A1* | 5/2004 | Cohen | A61B 5/316 600/411 |
| 2007/0213786 A1* | 9/2007 | Sackellares | A61N 1/36025 607/45 |
| 2008/0228100 A1 | 9/2008 | Navakatikyan | |
| 2011/0125046 A1 | 5/2011 | Burton et al. | |

OTHER PUBLICATIONS

Bellesi, M. et al., "Enhancement of sleep slow waves: underlying mechanisms and practical consequences", Frontiers in Systems Neuroscience, Oct. 2014.

H.-V. V Ngo, T. Martinetz, J. Born, and M. Molle, "Auditory Closed-Loop Stimulation of the Sleep Slow Oscillation Enhances Memory," Neuron, vol. 78, no. May, pp. 1-9, 2013.

Schabus, M. et al., "The Fate of Incoming Stimuli during NREM Sleep is Determined by Spindles and the Phase of the Slow Oscillation.," Front. Neurol., vol. 3, no. April, p. 40, Jan. 2012.

E. C. Landsness, M. R. Goldstein, M. J. Peterson, G. Tononi, and R. M. Benca, "Antidepressant effects of selective slow wave sleep deprivation in major depression: a high-density EEG investigation.," J. Psychiatr. Res., vol. 45, No. 8, pp. 1019-1026, Aug. 2011.

A. R. Møller, "Use of zero-phase digital filters to enhance brainstem auditory evoked potentials (BAEPs).," Electroencephalogr. Clin. Neurophysiol., vol. 71, No. 3, pp. 226-232, 1988.

* cited by examiner

US 11,253,673 B2

DETERMINING CORRECTED TIMING OF STIMULATION PROVIDED TO A SUBJECT DURING SLEEP

CROSS-REFERENCE TO PRIOR APPLICATIONS

This application is the U.S. National Phase application under 35 U.S.C. § 371 of International Application Serial No. PCT/EP2017/081840, filed on 7 Dec. 2017, which claims the benefit of U.S. Application Ser. No. 62/431,482, filed on 8 Dec. 2016. These applications are hereby incorporated by reference herein.

BACKGROUND

1. Field

The present disclosure pertains to a system and method for determining corrected timing of stimulation provided to a subject during a sleep session.

2. Description of the Related Art

Systems for monitoring sleep are known. Sensory stimulation during sleep is known. Sensory stimulation during sleep is often applied continuously and/or at intervals and intensities that do not correspond to sleeping patterns of a subject. The present disclosure overcomes deficiencies in prior art systems.

SUMMARY

Accordingly, one or more aspects of the present disclosure relate to a system configured to determine timing of stimulation provided to a subject during a sleep session. The system comprises one or more stimulators, one or more sensors, one or more hardware processors, and/or other components. The one or more stimulators are configured to provide stimulation to the subject. The one or more sensors are configured to generate output signals conveying information related to slow wave activity in the subject during the sleep session. The one or more hardware processors operatively communicate with the one or more stimulators and the one or more sensors. The one or more hardware processors are configured by machine-readable instructions to receive a raw signal from the one or more sensors; buffer a portion of the raw signal; determine a timing of slow wave events in the buffered portion of the raw signal, the timing of the slow wave events determined based on characteristics of the buffered portion of the raw signal; filter the raw signal to reduce noise artifacts and potential distortions in the raw signal; determine a timing of slow wave events in the filtered raw signal based on characteristics of the filtered raw signal, the slow wave events in the filtered raw signal corresponding to the slow wave events in the buffered portion of the raw signal; compare the timing of the slow wave events in the buffered portion of the raw signal to the timing of the slow wave events in the filtered raw signal; based on the comparison, determine a first correction factor associated with reducing slow wave activity in the subject and/or a second correction factor associated with enhancing slow wave activity in the subject; and control the one or more stimulators to adjust a timing of the stimulation provided to the subject during the sleep session based on the first correction factor to reduce slow wave sleep in the subject, and/or based on the second correction factor to enhance slow wave sleep in the subject.

Yet another aspect of the present disclosure relates to a method for determining timing of stimulation provided to a subject during a sleep session with a determination system. The system comprises one or more stimulators, one or more sensors, one or more hardware processors, and/or other components. The method comprises: providing, with the one or more stimulators, stimulation to the subject; generating, with the one or more sensors, output signals conveying information related to slow wave activity in the subject during the sleep session; receiving, with the one or more processors, a raw signal from the one or more sensors; buffering, with the one or more processors, a portion of the raw signal; determining, with the one or more processors, a timing of slow wave events in the buffered portion of the raw signal, the timing of the slow wave events determined based on characteristics of the buffered portion of the raw signal; filtering, with the one or more processors, the raw signal to reduce noise artifacts and potential distortions in the raw signal; determining, with the one or more processors, a timing of slow wave events in the filtered raw signal based on characteristics of the filtered raw signal, the slow wave events in the filtered raw signal corresponding to the slow wave events in the buffered portion of the raw signal; comparing, with the one or more hardware processors, the timing of the slow wave events in the buffered portion of the raw signal to the timing of the slow wave events in the filtered raw signal; based on the comparison, determining, with the one or more hardware processors, a first correction factor associated with reducing slow wave activity in the subject and/or a second correction factor associated with enhancing slow wave activity in the subject; and controlling, with the one or more hardware processors, the one or more stimulators to adjust a timing of the stimulation provided to the subject during the sleep session based on the first correction factor to reduce slow wave sleep in the subject, and/or based on the second correction factor to enhance slow wave sleep in the subject.

Still another aspect of present disclosure relates to a system for determining timing of stimulation provided to a subject during a sleep session. The system comprises: means for providing stimulation to the subject; means for generating output signals conveying information related to slow wave activity in the subject during the sleep session; means for receiving a raw signal from the one or more sensors; means for buffering a portion of the raw signal; means for determining a timing of slow wave events in the buffered portion of the raw signal, the timing of the slow wave events determined based on characteristics of the buffered portion of the raw signal; means for filtering the raw signal to reduce noise artifacts and potential distortions in the raw signal; means for determining a timing of slow wave events in the filtered raw signal based on characteristics of the filtered raw signal, the slow wave events in the filtered raw signal corresponding to the slow wave events in the buffered portion of the raw signal; means for comparing the timing of the slow wave events in the buffered portion of the raw signal to the timing of the slow wave events in the filtered raw signal; based on the comparison, means for determining a first correction factor associated with reducing slow wave activity in the subject and/or a second correction factor associated with enhancing slow wave activity in the subject; and means for controlling the means for providing stimulation to adjust a timing of the stimulation provided to the subject during the sleep session based on the first correction factor to reduce slow wave sleep in the subject, and/or based on the second correction factor to enhance slow wave sleep in the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
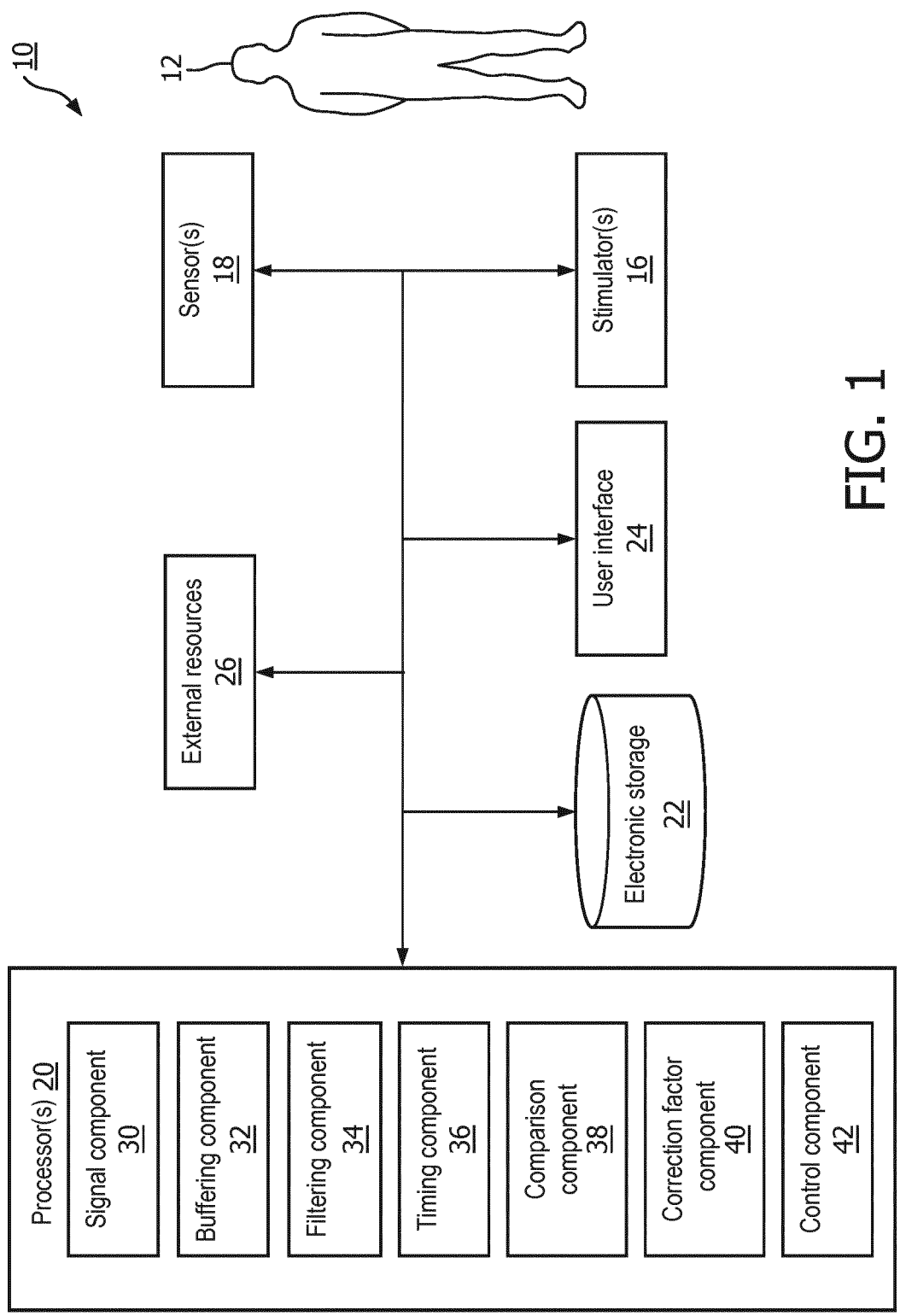
FIG. 1 illustrates a system for determining corrected timing of stimulation provided to a subject during a sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 for determining a corrected timing of stimulation provided to a subject 12 during a sleep session. An electroencephalogram (EEG) signal and/or other signals that convey information related to slow wave activity (SWA) in a subject (e.g., subject 12) often have low signal-to-noise ratios (SNR). Processing such signals (both in real-time and not real-time) requires filtering to improve the SNR. An EEG signal and/or other signals that convey information related to SWA are often sensitive to noise sources both internal (e.g., eye blinks, electro-dermal potentials, movements, etc.) and external (e.g., power-line interference and/or other electro-magnetic influences in the environment). Consequently, filtering of such signals is necessary to improve the SNR but comes at a cost of introducing signal distortions.

Filtering introduces shape and phase distortions in the EEG signal. Solutions for attenuating distortions during non-real-time processing exist (e.g., zero-phase filtering). However, typical filters that are applied to attempt to attenuate noisy components of the signal in real-time introduce phase distortions which can cause significant inaccuracies in the timing of detection of slow waves. Because of this, in typical systems, stimulation is not delivered at desired times. Solutions for attenuating distortions during real-time and/or near real-time processing of an EEG signal and/or other signals that convey information related to SWA are needed.

For example, sleep session management systems time stimulation according to specific phases and/or characteristics (as described below) of real-time and/or near real-time detected sleep slow waves in the EEG and/or other signals. Delivering auditory and/or other stimulation during slow wave sleep influences the amplitude of subsequent sleep slow waves. The nature of the influence depends on the timing of the stimulation with respect to the sleep slow wave phase and/or characteristics. When the stimulation happens in the vicinity of a slow wave positive peak the subsequent slow waves have a higher amplitude (e.g., they are enhanced). The enhancement effect is believed to be beneficial for increasing the restorative value of sleep. Delivering the stimulation in the vicinity of a slow wave negative peak may have a reducing effect (e.g., a decrease in amplitude) on the amplitude of the subsequent positive peak. This effect may be useful in situations where deprivation of slow wave sleep is sought (e.g., in the framework of depression relief). However, phase distortions of detected slow waves caused by filtering cause inaccuracies in the intended timing (e.g., relative to a peak of a given slow wave) of the stimulation.

Figure 2:
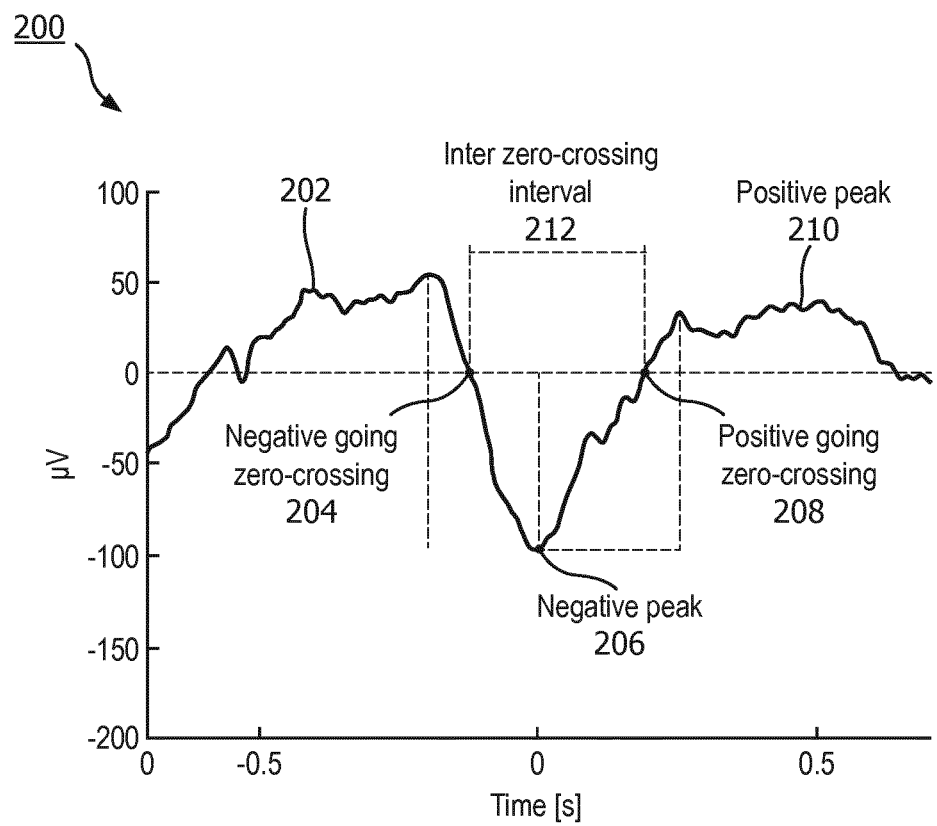
FIG. 2 illustrates a portion of an EEG signal that shows characteristics of a sleep slow wave.

By way of a non-limiting example, FIG. 2 illustrates a portion 200 of an EEG signal that shows characteristics of a sleep slow wave 202. Characteristics of sleep slow wave 202 are labeled in FIG. 2 including a negative going zero crossing 204, a negative peak 206, a positive going zero crossing 208, a positive peak 210, and an inter zero-crossing interval 212. In some embodiments, negative peak 206 comprises a local minima in the signal, positive peak 210 comprises a local maxima in the signal, negative going zero crossing 204 comprises a transition in the signal from positive peak 210 to negative peak 206, and positive going zero crossing 208 comprises a transition in the signal from negative peak 206 to positive peak 210. In some embodiments, inter zero crossing interval 212 is an amount of time between negative going zero crossing 204 and positive going zero crossing 208, and/or other amounts of time.

Figure 3:
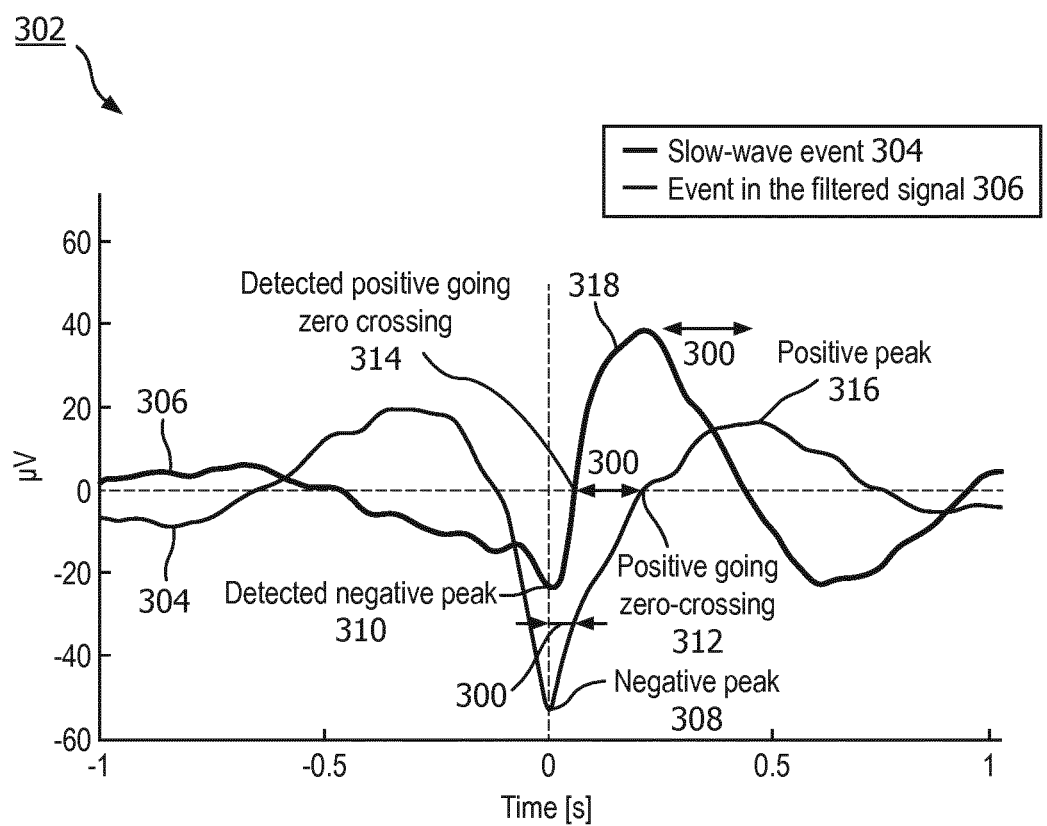
FIG. 3 illustrates distortions introduced by real-time filtering on an EEG signal that includes slow waves for a slow wave event.

FIG. 3 illustrates distortions 300 introduced by real-time filtering on the signal used to detect slow waves for a slow wave event 302. In FIG. 3, a first signal 304 corresponds to a slow wave detected on the EEG signal band-pass filtered with a zero-phase filtering in the frequency band from 0.8 to 40 Hz (this signal has therefore minor delays). A second signal 306 corresponds to the slow wave event in the filtered EEG that is processed in real-time. As shown in FIG. 3, the negative peaks 308 and 310, the positive going zero crossings 312 and 314, and the positive peaks 316 and 318 are not the same. This indicates how phase distortions of detected slow waves caused by filtering in typical prior art systems cause inaccuracies in the intended timing (e.g., relative to a peak of the slow wave shown in signal 304) of the stimulation.

Returning to FIG. 1, system 10 is configured to monitor the EEG and/or other signals of subject 12 during sleep, automatically and in real-time and/or near real-time detect deep sleep (e.g., slow wave sleep), and deliver auditory and/or other stimulation to enhance slow waves without causing sleep disturbances. System 10 is configured to automatically characterize the distortion introduced by real-time and/or near real-time applied filters and to adjust the timing of the stimulation accordingly. System 10 relies on the automatic and delayed detection of slow wave events (e.g., based on characteristics of the EEG signal) using a portion of the raw (unfiltered) EEG signal. Slow wave events may include and/or be related to slow waves, k-complexes, and/or other features of an EEG and/or other signals that are associated with and/or indicate deep and/or slow wave sleep in subject 12.

System 10 is configured to deliver stimulation at a desired time by comparing a raw (e.g., unfiltered) EEG signal and/or other signals that convey information related to SWA in subject 12 (e.g., similar to signal 304 in FIG. 3) to a filtered signal (e.g., similar to signal 306 in FIG. 3). System 10 is configured to adjust the timing of stimulation provided to subject 12 for the distortion introduced by such filtering. In some embodiments, (e.g., if stimulation is to occur after a positive-going zero-crossing), system 10 is configured to correct for the timing difference between the actual zero-crossing in the raw signal (e.g., 312 in FIG. 3) and a detected zero-crossing in the filtered signal (e.g., 314 in FIG. 3) with a slow wave enhancement correction factor. In some embodiments, (e.g., if the stimulation is to occur in the vicinity of a negative peak), system 10 is configured to correct for the timing difference between the actual negative peak in the raw signal (e.g., 308 in FIG. 3) and the detected negative peak in the filtered signal (e.g., 310 in FIG. 3) with a slow wave reduction correction factor.

System 10 is configured such that the slow wave enhancement and the slow wave reduction correction factors are not necessarily the same. This is because correction strategies based, for example, on the estimation of filter delays, and/or a single analysis of correlation would fail to accurately correct stimulation timing because these strategies would result in a single correcting factor. A single correction factor is also inadequate because the distortion induced by typical filtering depends on the particular spectral content of slow waves which can vary across subjects.

In some embodiments, system 10 includes one or more of a stimulator 16, a sensor 18, a processor 20, electronic storage 22, a user interface 24, external resources 26, and/or other components.

Stimulator 16 is configured to provide electric, magnetic, sensory, and/or other stimuli to subject 12. Stimulator 16 is configured to provide stimulation to subject 12 prior to a sleep session, during a sleep session, and/or at other times. For example, stimulator 16 may be configured to provide stimuli to subject 12 during deep (e.g., slow wave sleep) sleep in a sleep session to facilitate a transition to a lighter stage of sleep. As another example, stimulator 16 may be configured to provide stimulation to subject 12 to induce deeper sleep in subject 12 (e.g., facilitate a transition from a lighter stage of sleep). As a third example, stimulator 16 may be configured to provide stimuli to subject 12 to maintain a particular stage of sleep. In some embodiments, stimulator 16 may be configured such that maintaining sleep in a particular sleep stage and/or facilitating a transition between sleep stages includes inducing, increasing, enhancing, and/or decreasing sleep slow waves in subject 12.

Stimulator 16 is configured to maintain sleep in a particular sleep stage and/or facilitate transitions between sleep stages through non-invasive brain stimulation and/or other methods. The stimulation may include auditory stimulation, visual stimulation, somatosensory stimulation, electrical stimulation, magnetic stimulation, a combination of different types of stimulation, and/or other stimulation. The stimuli include odors, sounds, visual stimulation, touches, tastes, somatosensory stimulation, haptic, electrical, magnetic, and/or other stimuli. For example, acoustic tones may be provided to subject 12 to facilitate a transition from a deeper stage of sleep to a lighter stage of sleep or vice versa. Examples of stimulator 16 may include one or more of a music player, a tone generator, a collection of electrodes on the scalp of subject 12, a unit to deliver vibratory stimulation, a coil generating a magnetic field to directly stimulate the brain's cortex, light generators, a fragrance dispenser, and/or other devices. In some embodiments, stimulator 16 is configured to adjust the intensity, timing, and/or other parameters of the stimulation provided to subject 12.

Sensor 18 is configured to generate output signals conveying information related to brain activity of subject 12. The brain activity may be and/or be related to SWA in subject 12 and/or other characteristics of subject 12. Slow wave sleep and/or SWA may be observed and/or estimated by way of the EEG and/or other information. In some embodiments, SWA corresponds to the power of the EEG signal in the 0.5-4.0 Hz band. In some embodiments, this band is set to 0.5-4.5 Hz. SWA has a typical behavior throughout cyclic variations of a given sleep session. SWA increases during NREM sleep, declines before the onset of REM sleep, and remains low during REM sleep. SWA in successive NREM (e.g., slow wave sleep) episodes progressively decreases from one episode to the next. The SWA and/or brain activity of subject 12 may correspond to a specific sleep stage and/or stages of subject 12. Sleep stage(s) of subject 12 may be associated with REM sleep, NREM sleep, and/or other sleep. The sleep stage of subject 12 may be one or more of NREM stage N1, stage N2, stage N3, or stage N4 sleep, REM sleep, and/or other sleep stages. In some embodiments, stage N4 and/or N3 sleep may be and/or correspond to slow wave sleep. In some embodiments, stage N2, N3, and/or stage N4 sleep may be slow wave sleep. In some embodiments, slow waves may not be present throughout a whole N3 period, for example, but it may be significantly more likely that such slow waves are present during N3. Slow waves may also be present (although to a lesser extent) during N2, for example.

Sensor 18 may comprise one or more sensors that measure such parameters directly. For example, sensor 18 may include EEG electrodes configured to detect electrical activity along the scalp of subject 12 resulting from current flows within the brain of subject 12. Sensor 18 may comprise one or more sensors that generate output signals conveying information related to brain activity of subject 12 indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, temperature of subject 12, and/or other characteristics of subject 12. In some embodiments, the one or more sensors comprise one or more of the EEG electrode, an electrooculogram (EOG) electrode, an actigraphy sensor, an electrocardiogram (EKG) electrode, a respiration sensor, a pressure sensor, a vital signs camera, a photoplethysmogram (PPG) sensor, a functional near infrared sensor (fNIR), a thermometer, and/or other sensors. Although sensor 18 is illustrated at a single location near subject 12, this is not intended to be limiting. Sensor 18 may include sensors disposed in a plurality of locations, such as for example, within (or in communication with) stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of a signal component 30, a buffering component 32, a filtering component 34, a timing component 36, a comparison component 38, a correction factor component 40, a control component 42, and/or other components. Processor 20 may be configured to execute components 30, 32, 34, 36, 38, 40, and/or 42 by software; hardware; firmware; some combination of software, hardware, and/or firmware; and/or other mechanisms for configuring processing capabilities on processor 20.

It should be appreciated that although components 30, 32, 34, 36, 38, 40, and 42 are illustrated in FIG. 1 as being co-located within a single processing unit, in embodiments in which processor 20 comprises multiple processing units, one or more of components 30, 32, 34, 36, 38, 40, and/or 42 may be located remotely from the other components. The description of the functionality provided by the different components 30, 32, 34, 36, 38, 40, and/or 42 described below is for illustrative purposes, and is not intended to be limiting, as any of components 30, 32, 34, 36, 38, 40, and/or 42 may provide more or less functionality than is described. For example, one or more of components 30, 32, 34, 36, 38, 40, and/or 42 may be eliminated, and some or all of its functionality may be provided by other components 30, 32, 34, 36, 38, 40, and/or 42. As another example, processor 20 may be configured to execute one or more additional components that may perform some or all of the functionality attributed below to one of components 30, 32, 34, 36, 38, 40, and/or 42.

Signal component 30 is configured to receive one or more raw signals from one or more sensors 18. In some embodiments, a raw signal comprises a signal that has not been filtered and/or otherwise altered so that it includes less and/or different information than generated by the particular sensor and/or sensors 18 that were the source of the signal. In some embodiments, signal component 30 may receive the one or more raw signals from sensors 18 wirelessly and/or via wires. In some embodiments, signal component 30 may receive raw signals substantially continuously from sensors 18, at predetermined intervals, and/or at other times.

Buffering component 32 is configured to buffer a portion of a raw signal received by signal component 30. Buffering comprises electronically storing the portion of the raw signal in an electronic memory (e.g., electronic storage 22) and/or in other devices. The electronic memory may be a component of system 10, part of external resources 26, and/or included in other devices. In some embodiments, the electronic memory may comprise cloud storage. In some embodiments, the buffered signal may be temporarily stored for a predetermined period of time and/or until occurrence of a predetermined event that allows system 10 to function as described herein. In some embodiments, buffering component 32 is configured to buffer up to about ten minutes of the raw signal. In some embodiments, buffering component 32 is configured to buffer between about ten seconds and about ten minutes of the raw signal. In some embodiments, buffering component 32 is configured to buffer between about three minutes and about five minutes of the raw signal.

In some embodiments, the buffering begins responsive to detection of N2 sleep. In such embodiments, buffering component 32 may be configured such that detection of N2 sleep comprises setting a threshold on the power (e.g., in RMS (root mean square) units over a 10 second long window) in the delta band (e.g., 0.5 to 4 Hz) of the EEG and/or setting other thresholds. In some embodiments, the value of this threshold may be 8 (for example), and if the delta RMS power is above this threshold for at least 75 seconds, then the sleep stage after the 75 second long interval is determined to be at least N2 (if sleep deepens further the stage would become N3 which would be more beneficial for system 10). As described above, the minimum duration of the raw signal that is buffered is about 10 seconds (e.g., to ensure the detection of at least one slow wave and/or k-complex in the buffered portion of the raw signal). Increasing the duration of the buffer increases the precision (e.g., proportionally to the square root of the duration) of the estimation of the correction factors and/or time adjustment parameters $\Delta_1$, and $\Delta_2$ (described below).

In some embodiments, buffering component 32 is configured such that in addition to and/or instead of the buffering depending on the sleep state (as described in the previous paragraph), buffering component 32 is configured to begin buffering the raw signal responsive to the detection of negative peaks (e.g., as described below) in the EEG signal and/or other signals that convey information related to slow wave activity in subject 12 with an amplitude lower than about −60 microvolts (for example) and with a duration between detected zero-crossings that is in the interval between about 0.2 (for example) and about 0.9 (for example) seconds. In this embodiment, the buffering depends on the detection of slow-wave like events (e.g., as described below).

Filtering component 34 is configured to filter the raw signal received by signal component 30. The raw signal is filtered to reduce noise artifacts in the raw signal and/or for other reasons. In some embodiments, filtering component 34 is configured such that filtering occurs separately from buffering, but substantially concurrently with buffering, and/or at other times. In some embodiments, filtering component 34 is configured such that the raw signal is band-pass filtered with a zero-phase filtering in the frequency band from 0.8 to 40 Hz, for example. In some embodiments, filtering comprises a single-pole high-pass filter (e.g., cut-off frequency of 0.3 Hz). In some embodiments, filtering comprises a third order high pass IIR filter (e.g., cut-off frequency of 0.8 Hz). In general, high-pass filters may be used because they help removing any DC drift that can be (often) present in the EEG signal. In some embodiments, filtering component 34 comprises and/or communicates with a high-pass analog filter (e.g., implemented in hardware).

Timing component 36 is configured to detect and determine a timing of slow wave events in the buffered portion of the signal. Slow wave events may include and/or be related to slow waves, k-complexes, and/or other slow wave events. In some embodiments, such events include zero-crossings (e.g., negative going and/or positive going), negative peaks, positive peaks, and/or other events as described herein. The timing of the slow wave events in the buffered portion of the raw signal is determined based on characteristics of the buffered portion of the raw signal, and/or other information. The characteristics of the buffered portion of the raw signal comprise negative going zero crossings, negative peaks, positive going zero crossings, positive peaks, an inter zero crossing interval, and/or other characteristics of the buffered portion of the raw signal. In some embodiments, determining the timing of slow wave events in the buffered portion of the raw signal comprises aligning and averaging segments of the buffered raw signal around negative peaks in the buffered raw signal. In some embodiments, averaging comprises time lock averaging, event lock averaging, negative peak lock averaging, and/or other averaging.

Timing component 36 does not need information about the sleep stages in subject 12 to detect and/or determine timing of slow wave events in the buffered portion of the signal. In some embodiments, timing component 36 detects and/or determines the timing of slow wave events by identifying EEG (and/or other signals that convey information related to SWA in subject 12) events that have predetermined elements. The predetermined elements include (1) a negative-going zero-crossing, (2) a negative peak with an (absolute) amplitude of at least about 30 microvolts, (3) a positive going zero-crossing which occurs between about 100 and about 900 milliseconds after the detected negative-going zero-crossing, and/or other elements. In some embodiments, this may be termed "non-causal detection" (e.g., buffering and then analyzing the buffered signal). These three elements are not intended to be limiting. System 10 may use any signal elements that facilitate detection and/or determination of timing of slow wave events in an EEG signal and/or any signal that conveys information related to SWA in subject 12.

Because this detection happens in a non-causal mode, the duration and amplitude parameters can be accurately evaluated and compared to thresholds. The accuracy is relative to real-time detection. In real-time detection, the causally filtered signal would have distortions and because of that, the comparison to thresholds (which, for example, may be extracted from literature and/or established from offline analyses) is less accurate. The thresholds may correspond to negative peaks, an interval between zero crossings, and/or other characteristics. In some embodiments, timing component 36 is configured to apply a zero-phase filer on the raw EEG signal in the frequency band (0.1 to 40 Hz) to enhance detection of the slow wave like events.

In some embodiments, timing component 36 is configured to automatically detect the phase shift in a signal by identifying the instantaneous frequency of a slow wave itself. For example, timing component 36 may be configured such that a decomposition method may provide for frequency estimation and an empirical or look up delay based on frequency content may be established. In general, the interval between zero-crossings, for example, may be used as an estimate of the instantaneous slow-wave frequency. One may empirically tabulate delays for different values of instantaneous frequencies (e.g., 20 ms for 0.8 Hz, 40 ms for 0.9 Hz, 50 ms for 1 Hz, etc.).

Figure 4:
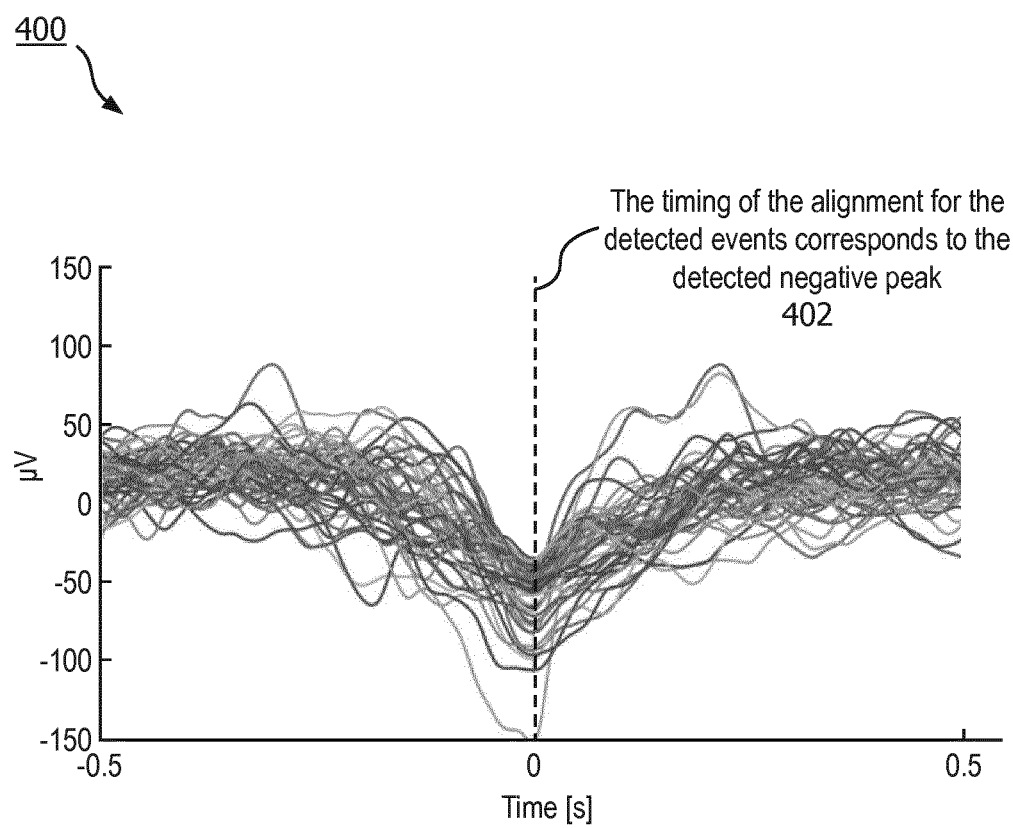
FIG. 4 illustrates aligning several segments of a buffered raw signal around negative peaks in the buffered raw signal.

FIG. 4 illustrates aligning several segments 400 of the buffered raw signal around negative peaks 402 in the buffered raw signal. The individual aligned segments correspond to different slow wave events detected in the buffered raw signal. In some embodiments, timing component 36 (FIG. 1) is configured such that segments (e.g., about one second long as shown in FIG. 4 but this is not intended to be limiting) of the buffered raw signal around the detected negative peaks are determined, aligned based on the position of the detected negative peaks, and then averaged. In FIG. 4, the negative peaks of segments 400 are used as reference points. The choice of negative peaks as reference points is a non-restrictive example but is used here because the negative peak is a prominent mark in a slow wave.

Returning to FIG. 1, the slow wave events in the buffered portion of the raw signal correspond to slow wave events detected in the filtered raw signal. Timing component 36 is also configured to determine a timing of slow wave events in the filtered raw signal. Like the detection and determination of the slow wave events in the buffered portion of the raw signal, the timing of slow wave events in the filtered raw signal is determined based on characteristics of the filtered raw signal and/or other information. The characteristics of the filtered raw signal comprise negative going zero crossings, negative peaks, positive going zero crossings, positive peaks, an inter zero crossing interval, and/or other characteristics in the filtered raw signal. In some embodiments, determining the timing of slow wave events in the filtered raw signal comprises aligning and averaging segments of the filtered raw signal around negative peaks in the filtered raw signal (e.g., similar to what is shown in FIG. 4 for the buffered raw signal). In some embodiments, averaging comprises time lock averaging, event lock averaging, negative peak lock averaging, and/or other averaging that is similar to and/or the same as what is described above for the buffered portion of the raw signal.

Figure 5:
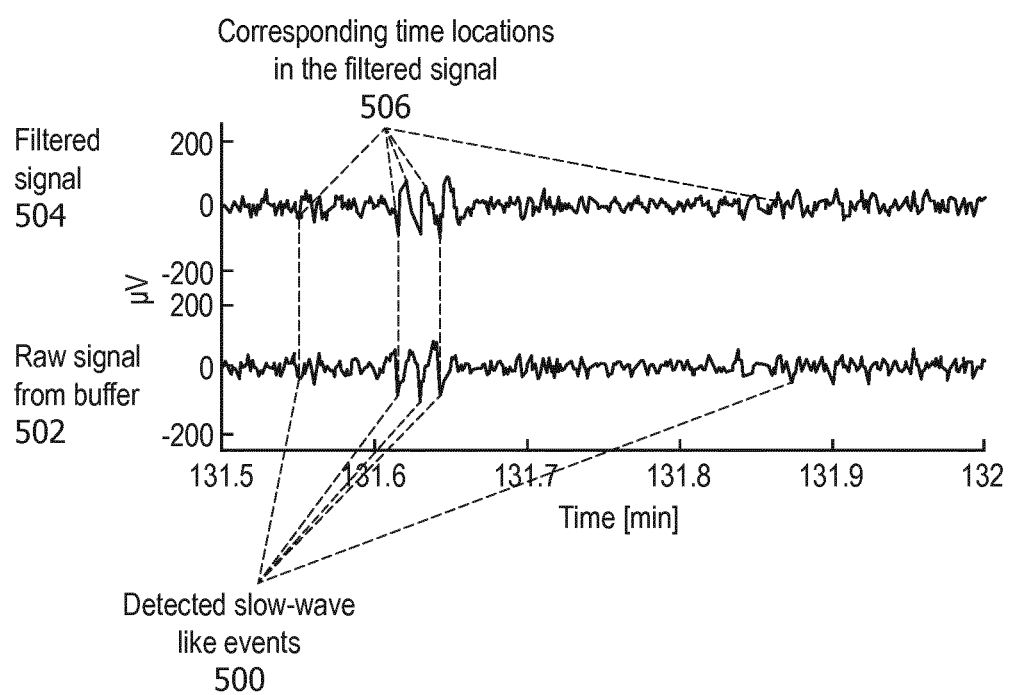
FIG. 5 illustrates a comparison of the timing of characteristics of detected slow wave events in a buffered portion of a raw signal with corresponding time locations shown in a filtered signal.

Comparison component 38 is configured to compare the timing of slow wave events in the buffered signal to the timing of slow wave events in the filtered signal. The timing of the detected events is used to determine the correction factors (e.g., as described below). The average on the raw signal results in a shape typical of a sleep slow wave. The timing of the characteristics of the average shape of the buffered portion of the raw signal is compared to the timing of corresponding characteristics of corresponding slow wave events in the filtered signal. For example, FIG. 5 illustrates a comparison of the timing of characteristics of detected slow wave events 500 in a raw buffered signal 502 with corresponding time locations 506 shown in a filtered signal 504. In FIG. 5, the timing of the characteristics (e.g., peaks, valleys, zero-crossings) of signal 502 do not align with corresponding characteristics of signal 504 (this is described and illustrated in greater/enlarged detail below related to FIG. 6).

Returning to FIG. 1, correction factor component 40 is configured to determine a correction factor associated with reducing slow wave activity, a correction factor associated with enhancing slow wave activity, and/or other correction factors. The correction factors are determined based on the comparison and/or other information. In some embodiments, the correction factor associated with reducing slow wave activity is associated with a timing difference between corresponding negative peaks in the filtered raw signal and the buffered portion of the raw signal. In some embodiments, the correction factor associated with enhancing slow wave activity is associated with a timing difference between corresponding positive zero-crossings, positive peaks, and/or other characteristics in the filtered raw signal and the buffered portion of the raw signal.

Figure 6:
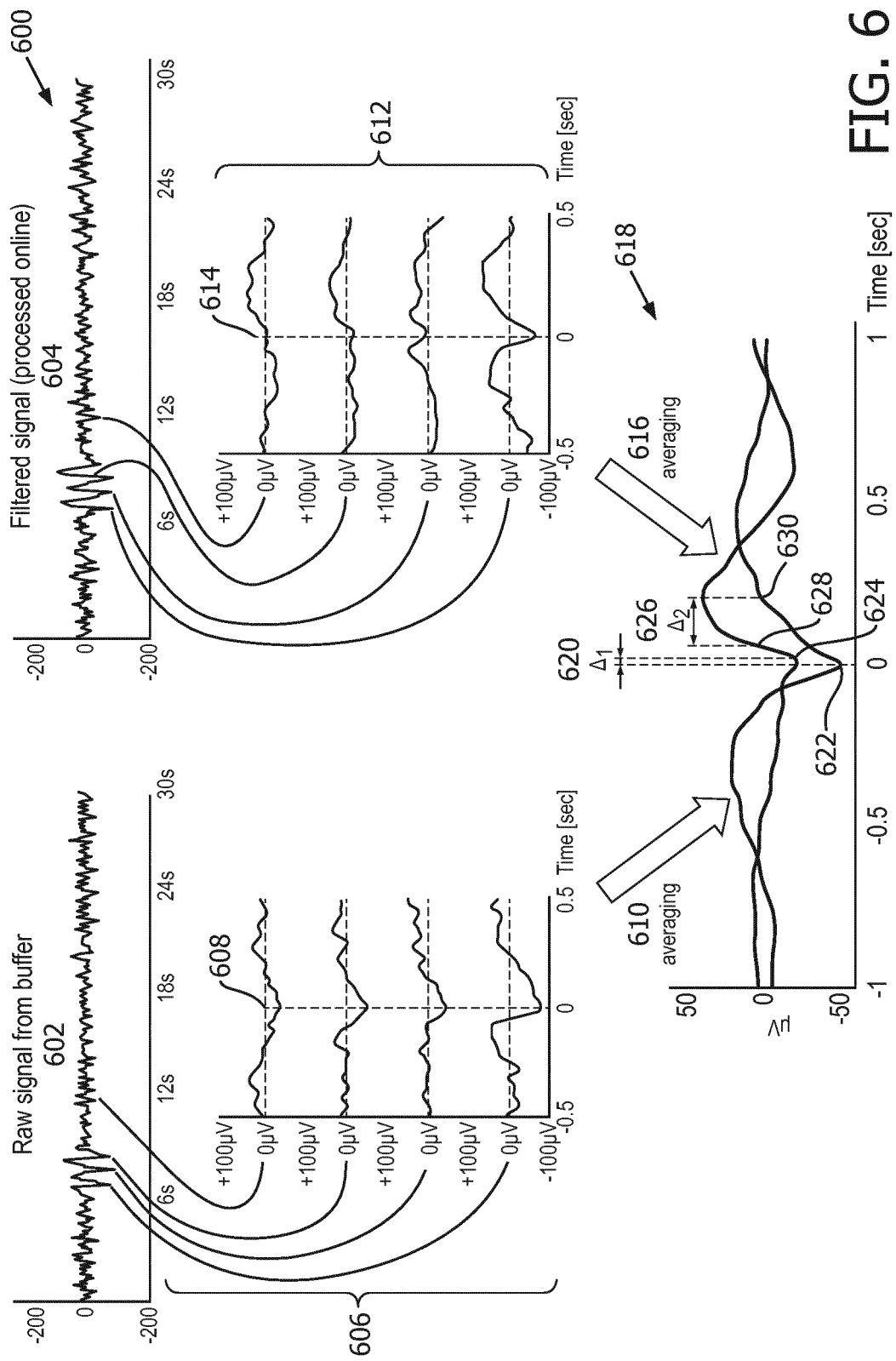
FIG. 6 illustrates a more detailed view of the comparison between slow wave event related portions of the buffered portion of the raw signal and the filtered signal.

In some embodiments, determining one or more of the correction factors is based on the mapping of the timing of the detected slow wave events in the buffered portion of the raw signal to the filtered signal. As described above (and shown in FIG. 5), because of the delay and distortion introduced by the filter, the detected negative peaks do not coincide between the raw signal and the filtered signal. FIG. 6 illustrates a more detailed view 600 of the comparison between slow wave event related portions of the buffered portion of the raw signal 602 and the filtered raw signal 604. As shown in FIG. 6, individual sections 606 of signal 602 that include negative peaks in signal 602 are aligned 608 and averaged 610 (e.g., by timing component 36 as shown in FIG. 1 and described above). Similarly, individual sections 612 of signal 604 that include negative peaks in signal 604 are aligned 614 and averaged 616 (e.g., also by timing component 36 as shown in FIG. 1 and described above). The comparison (e.g., by comparison component 38 shown in FIG. 1 and described above) between these two averaged sections is shown in chart 618 of FIG. 6.

As shown in chart 618 of FIG. 6, in some embodiments, correction factor component 40 (FIG. 1) is configured to determine two time differences. The first of the determined time differences is the time difference 620 ($\Delta_1$) between the two detected averaged negative peaks 622 and 624. The second of the determined time differences is the time difference 626 ($\Delta_2$) between the two detected positive going zero-crossings 628 and 630. In some embodiments, correction factor component 40 is configured such that these time differences are the determined correction factors. For example, in some embodiments, time difference 620 ($\Delta_1$) between the two detected averaged negative peaks 622 and 624 is the correction factor associated with reducing slow wave activity. The time difference 626 ($\Delta_2$) between the two detected positive going zero-crossings is the correction factor associated with enhancing slow wave activity. In some embodiments, correction factor component 40 determines the correction factors based on these time differences by performing other mathematical operations on the determined differences, combining the determined differences with other values such as offsets and/or constants, and/or performing other operations.

Returning to FIG. 1, it should be noted that the description of the determination of two time differences and/or correction factors is not intended to be limiting. There may be embodiments where only one time difference and/or correction factor is determined by system 10 (e.g., only the time difference and/or correction factor associated with reducing SWA, or only the time difference and/or correction factor associated with enhancing SWA), and/or embodiments where more than two time differences and/or correction factors are determined by system 10.

Control component 42 is configured to monitor the EEG and/or other signals from sensors 18 for subject 12 during sleep, automatically and in real-time and/or near real-time detect deep sleep (e.g., slow wave sleep), and deliver auditory and/or other stimulation to enhance slow waves without causing sleep disturbances (e.g., based on a predetermined therapy regime that specifies power band and/or other thresholds for sleep stage detection and/or timing of stimulation). Control component 42 is configured to control the stimulation based on one or both of the correction factors. The one or more stimulators 16 are controlled to adjust a timing of the stimulation provided to subject 12 during the sleep session based on the correction factor associated with reducing SWA to reduce slow wave sleep in subject 12, and/or based on the correction factor associated with enhancing SWA in subject 12 to enhance slow wave sleep in the subject. For example, if the desired time for stimulation is T milliseconds after a negative peak, the stimulation is adjusted by T+ (or − depending on the direction of the shift) $\Delta_1$ milliseconds. If the desired time for stimulation is T milliseconds after a positive going zero-crossing, the stimulation is adjusted by T+ (or − depending on the direction of the shift) $\Delta_2$ milliseconds.

Figure 7:
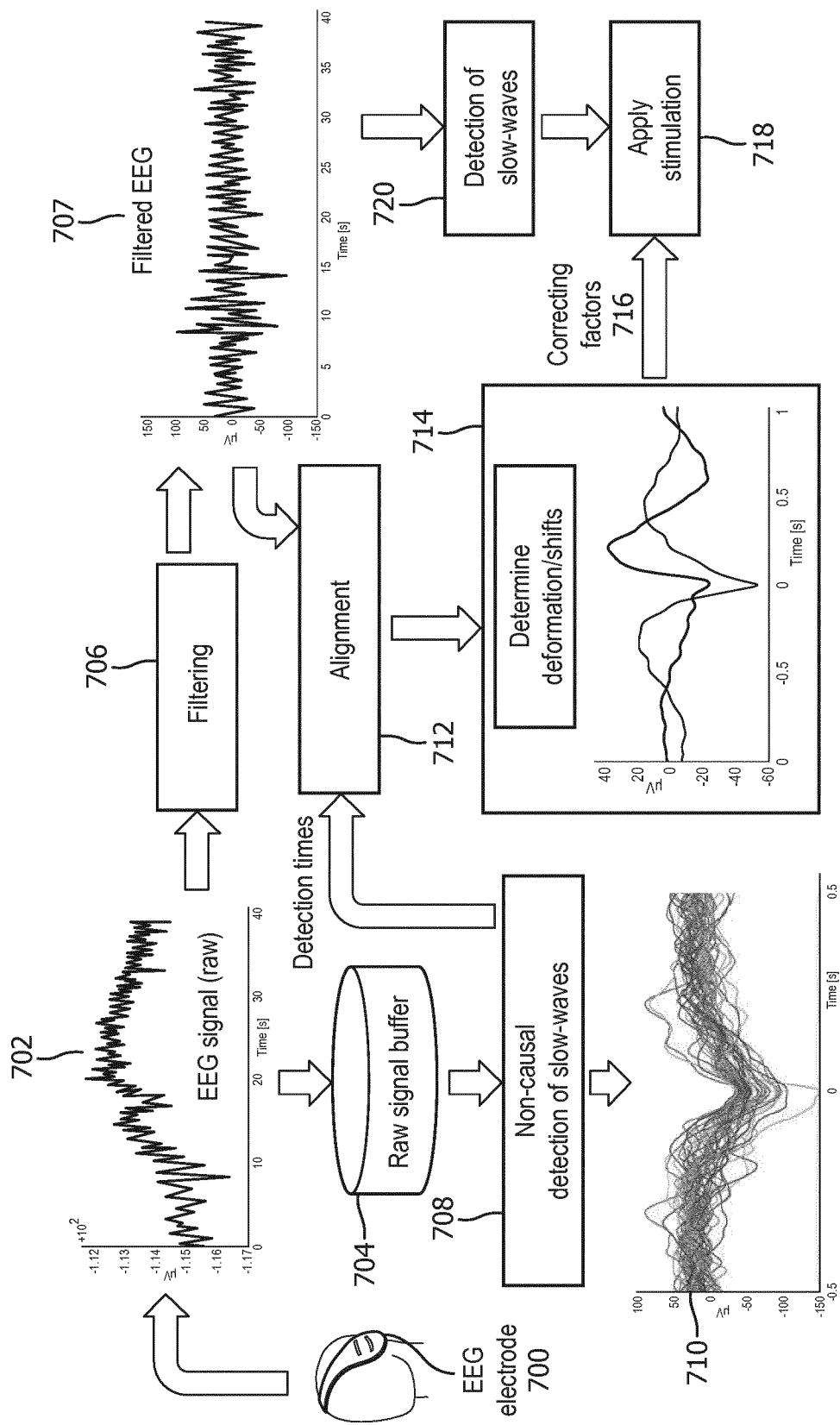
FIG. 7 illustrates a summary of operations performed by the system.

By way of a non-limiting example, operations performed by system 10 are graphically summarized in FIG. 7. As shown in FIG. 7, EEG electrodes (e.g., sensors 18 shown in FIG. 1) generate a raw EEG signal 702. Raw EEG signal 702 is buffered 704 (e.g., by buffering component 32), and (separately) filtered 706 (e.g., by filtering component 34) to produce a filtered signal 707. In some embodiments, buffering 704 and filtering 706 happens substantially simultaneously and/or at other times. Non-causal detection (e.g., as described above) 708 of slow waves and/or slow wave events is performed on the buffered portion of the raw signal (e.g., by timing component 36). Non-causal detection comprises segmenting, aligning, and averaging 710 portions of the buffered raw signal (e.g., based on the locations of the negative peaks and/or other information). At an operation 712, corresponding aligned and averaged slow wave events (e.g., slow waves, k-complexes, etc.) in the buffered portion of the raw signal and the filtered signal are compared and/or aligned (e.g., by comparison component 38). Time shifts of characteristics (e.g., negative peaks, positive going zero-crossings, and/or other characteristics) in the compared signals are identified 714 and one or more correction factors 716 are determined based on the time shifts. The correction factors may include a correction factor associated with reducing SWA, a correction factor associated with enhancing SWA, and/or other correction factors. In some embodiments, the correction factors are the time shifts themselves. Finally, stimulation delivered 718 to the subject is controlled based on slow waves detected 720 in filtered signal 707 and one or more of the correction factors 716.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to (e.g., a target wake-up moment) and receive information from system 10. This enables data, cues, results, and/or instructions and any other communicable items, collectively referred to as "information," to be communicated between a user (e.g., subject 12) and one or more of stimulator 16, sensor 18, processor 20, and/or other components of system 10. For example, an EEG may be displayed to a caregiver via user interface 24. As another example, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

External resources 26 includes sources of information (e.g., databases, websites, etc.), external entities participating with system 10 (e.g., a medical records system of a health care provider), medical and/or other equipment (e.g., audio and/or visual recording devices, etc.) configured to communicate with and/or be controlled by system 10, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. For example, in some embodiments, external resources 26 include one or more external databases that store information related to subject 12 and/or a population of demographically similar to subject 12. In some implementations, some or all of the functionality attributed herein to external resources 26 may be provided by resources included in system 10. External resources 26 may be configured to communicate with processor 20, user interface 24, sensor 18, electronic storage 22, and/or other components of system 10 via wired and/or wireless connections, via a network (e.g., a local area network and/or the internet), via cellular technology, via Wi-Fi technology, and/or via other resources.

In FIG. 1, stimulator 16, sensor 18, processor 20, electronic storage 22, and user interface 24 are shown as separate entities. This is not intended to be limiting. Some and/or all of the components of system 10 and/or other components may be grouped into one or more singular devices. For example, these components may be included in a headset and/or headband worn by subject 12 during sleep. This arrangement of the components of system 10 is not intended to be limiting. The components of system 10 may be arranged in any manner that allows them to function as described herein.

Figure 8:
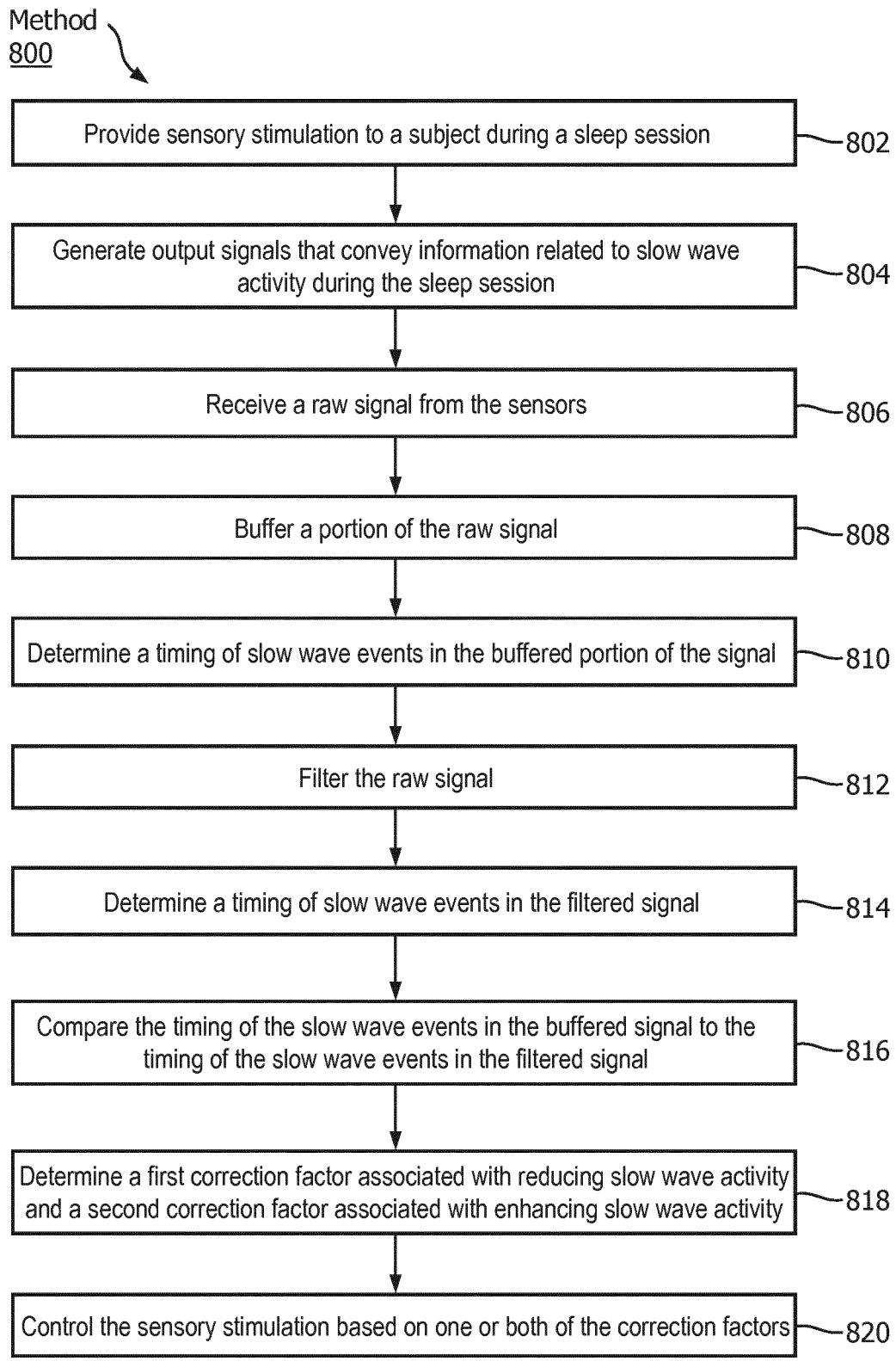
FIG. 8 illustrates a method for determining corrected timing of stimulation provided to a subject during a sleep session.

FIG. 8 illustrates a method 800 for determining corrected timing of stimulation provided to a subject during a sleep session with a determination system. The system comprises one or more stimulators, one or more sensors, one or more hardware processors, and/or other components. The one or more hardware processors are configured to execute computer program components. The computer program components comprise a signal component, a buffering component, a filtering component, a timing component, a comparison component, a correction factor component, a control component, and/or other components. The operations of method 800 presented below are intended to be illustrative. In some embodiments, method 800 may be accomplished with one or more additional operations not described, and/or without one or more of the operations discussed. Additionally, the order in which the operations of method 800 are illustrated in FIG. 8 and described below is not intended to be limiting.

In some embodiments, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/ or software to be specifically designed for execution of one or more of the operations of method 800.

At an operation 802, stimulation is provided to the subject during a sleep session. In some embodiments, operation 802 is performed by a stimulator the same as or similar to stimulator 16 (shown in FIG. 1 and described herein).

At an operation 804, output signals conveying information related to slow wave activity in the subject are generated during the sleep session. In some embodiments, operation 804 is performed by one or more sensors the same as or similar to sensors 18 (shown in FIG. 1 and described herein).

At an operation 806, a raw signal is received from the sensors. In some embodiments, operation 806 is performed by a processor component the same as or similar to signal component 30 (shown in FIG. 1 and described herein).

At an operation 808, a portion of the raw signal is buffered. In some embodiments, operation 808 is performed by a processor component the same as or similar to buffering component 32 (shown in FIG. 1 and described herein).

At an operation 810, a timing of slow wave events in the buffered portion of the signal is determined. The timing of the slow wave events in the buffered portion of the signal is determined based on characteristics of the buffered portion of the raw signal, and/or other information. In some embodiments, determining the timing of slow wave events in the buffered portion of the raw signal comprises aligning and averaging segments of the buffered portion of the raw signal around negative peaks in the buffered portion of the raw signal. In some embodiments, averaging comprises time lock averaging, event lock averaging, negative peak lock averaging, and/or other averaging. In some embodiments, operation 810 is performed by a processor component the same as or similar to timing component 36 (shown in FIG. 1 and described herein).

At an operation 812, the raw signal is filtered. The raw signal is filtered to reduce noise artifacts in the raw signal and/or for other reasons. In some embodiments, operation 812 is performed by a processor component the same as or similar to filtering component 34 (shown in FIG. 1 and described herein).

At an operation 814, a timing of slow wave events in the filtered raw signal is determined. The timing of slow wave events in the filtered raw signal is determined based on characteristics of the filtered raw signal and/or other information. The characteristics of the buffered portion of the raw signal and the filtered raw signal comprise negative going zero crossings, negative peaks, positive going zero crossings, positive peaks, and/or other characteristics. In some embodiments, the negative peaks comprise local minima in the signals, the positive peaks comprise local maxima in the signals, the negative going zero crossings comprise transitions in the signals from the positive peaks to the negative peaks, and the positive going zero crossings comprise transitions in the signals from the negative peaks to the positive peaks. In some embodiments, determining the timing of slow wave events in the filtered raw signal comprises aligning and averaging segments of the filtered raw signal around negative peaks in the filtered raw signal. In some embodiments, averaging comprises time lock averaging, event lock averaging, negative peak lock averaging, and/or other averaging. The slow wave events in the filtered raw signal correspond to the slow wave events in the buffered portion of the raw signal. In some embodiments, operation 814 is performed by a processor component the same as or similar to timing component 36 (shown in FIG. 1 and described herein).

At an operation 816, the timing of slow wave events in the buffered signal is compared to the timing of slow wave events in the filtered signal. In some embodiments, operation 816 is performed by a processor component the same as or similar to comparison component 38 (shown in FIG. 1 and described herein).

At an operation 818, a first correction factor associated with reducing slow wave activity and/or a second correction factor associated with enhancing slow wave activity are determined. The first and/or second correction factors are determined based on the comparison and/or other information. In some embodiments, the first correction factor is associated with a timing difference between corresponding negative peaks in the filtered raw signal and the buffered portion of the raw signal, and the second correction factor is associated with a timing difference between corresponding positive zero-crossings in the filtered raw signal and the buffered portion of the raw signal. In some embodiments, operation 818 is performed by a processor component the same as or similar to correction factor component 40 (shown in FIG. 1 and described herein).

At an operation 820, the stimulation is controlled based on one or both of the correction factors. The one or more stimulators are controlled to adjust a timing of the stimulation provided to the subject during the sleep session based on the first correction factor to reduce slow wave sleep in the subject, and/or based on the second correction factor to enhance slow wave sleep in the subject. In some embodiments, operation 820 is performed by a processor component the same as or similar to control component 42 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system configured to adjust timing of stimulation provided to a subject during a sleep session, the system comprising:
one or more stimulators configured to provide stimulation to the subject;
one or more sensors configured to generate output signals conveying information related to brain activity of the subject during the sleep session, the brain activity comprising slow wave activity in the subject during the sleep session; and one or more hardware processors operatively communicating with the one or more stimulators and the one or more sensors, the one or more hardware processors configured by machine-readable instructions to:
  receive a raw signal from the one or more sensors;
  buffer a portion of the raw signal, the buffered portion having one or more buffered portion characteristics;
  determine a timing of slow wave events in the buffered portion of the raw signal, the timing of the slow wave events determined based on the one or more buffered portion characteristics of the buffered portion of the raw signal;
  filter the raw signal to reduce noise artifacts and distortions in the raw signal, the filtered raw signal having one or more filtered raw signal characteristics;
  determine a timing of slow wave events in the filtered raw signal based on the one or more filtered raw signal characteristics of the filtered raw signal, the slow wave events in the filtered raw signal corresponding to the slow wave events in the buffered portion of the raw signal;
  compare the timing of the slow wave events in the buffered portion of the raw signal to the timing of the slow wave events in the filtered raw signal;
  based on the comparison, determine a first correction factor associated with reducing slow wave activity in the subject and/or a second correction factor associated with enhancing slow wave activity in the subject; and
  control the one or more stimulators to adjust a timing of the stimulation provided to the subject during the sleep session based on the first correction factor to reduce slow wave sleep in the subject, and/or based on the second correction factor to enhance slow wave sleep in the subject.

2. The system of claim 1, wherein the one or more hardware processors are configured such that the one or more buffered portion characteristics of the buffered portion of the raw signal comprise first negative going zero crossings, first negative peaks, first positive going zero crossings, and first positive peaks, and the one or more filtered raw signal characteristics of the filtered raw signal comprise second negative going zero crossings, second negative peaks, second positive going zero crossings, and second positive peaks.

3. The system of claim 2, wherein the one or more hardware processors are configured such that the first negative peaks comprise local minima in the buffered portion of the raw signal and the second negative peaks comprise local minima in the filtered raw signal, the first positive peaks comprise local maxima in the buffered portion of the raw signal and the second positive peaks comprise local maxima in the filtered raw signal, the first negative going zero crossings comprise transitions in the buffered portion of the raw signal from the first positive peaks to the first negative peaks and the second negative going zero crossings comprise transitions in the filtered raw signal from the second positive peaks to the second negative peaks, and the first positive going zero crossings comprise transitions in the buffered portion of the raw signal from the first negative peaks to the first positive peaks and the second positive going zero crossings comprise transitions in the filtered raw signal from the second negative peaks to the second positive peaks.

4. The system of claim 2, wherein the one or more hardware processors are configured such that the first correction factor is associated with a timing difference between corresponding second negative peaks in the filtered raw signal and the first negative peaks in the buffered portion of the raw signal, and the second correction factor is associated with a timing difference between corresponding second positive zero-crossings in the filtered raw signal and the first positive zero-crossings in the buffered portion of the raw signal.

5. The system of claim 2, wherein the one or more hardware processors are configured such that:
  determining the timing of slow wave events in the buffered portion of the raw signal comprises aligning and averaging segments of the buffered portion of the raw signal around the first negative peaks in the buffered portion of the raw signal; and
  determining the timing of slow wave events in the filtered raw signal comprises aligning and averaging segments of the filtered raw signal around the second negative peaks in the filtered raw signal.

6. The system of claim 5, wherein the one or more hardware processors are configured such that averaging comprises time lock averaging, event lock averaging, or negative peak lock averaging.

7. The system of claim 1, wherein the one or more sensors are configured such that the output signals comprise an electroencephalogram (EEG) output signal, and the information in the output signals comprises slow waves and/or k-complexes.

8. A method for adjusting timing of stimulation provided to a subject during a sleep session with a determination system, the system comprising one or more stimulators, one or more sensors, and one or more hardware processors, the method comprising:
  providing, with the one or more stimulators, stimulation to the subject;
  generating, with the one or more sensors, output signals conveying information related to brain activity of the subject during the sleep session, the brain activity comprising slow wave activity in the subject during the sleep session;
  receiving, with the one or more processors, a raw signal from the one or more sensors;
  buffering, with the one or more processors, a portion of the raw signal, the buffered portion having one or more buffered portion characteristics;
  determining, with the one or more processors, a timing of slow wave events in the buffered portion of the raw signal, the timing of the slow wave events determined based on the one or more buffered portion characteristics of the buffered portion of the raw signal;
  filtering, with the one or more processors, the raw signal to reduce noise artifacts and distortions in the raw signal, the filtered raw signal having one or more filtered raw signal characteristics;
  determining, with the one or more processors, a timing of slow wave events in the filtered raw signal based on the one or more filtered raw signal characteristics of the filtered raw signal, the slow wave events in the filtered raw signal corresponding to the slow wave events in the buffered portion of the raw signal;
  comparing, with the one or more hardware processors, the timing of the slow wave events in the buffered portion of the raw signal to the timing of the slow wave events in the filtered raw signal;

based on the comparison, determining, with the one or more hardware processors, a first correction factor associated with reducing slow wave activity in the subject and/or a second correction factor associated with enhancing slow wave activity in the subject; and controlling, with the one or more hardware processors, the one or more stimulators to adjust a timing of the stimulation provided to the subject during the sleep session based on the first correction factor to reduce slow wave sleep in the subject, and/or based on the second correction factor to enhance slow wave sleep in the subject.

9. The method of claim 8, wherein the one or more buffered portion characteristics of the buffered portion of the raw signal comprise first negative going zero crossings, first negative peaks, first positive going zero crossings, and first positive peaks, and the one or more filtered raw signal characteristics comprise second negative going zero crossings, second negative peaks, second positive going zero crossings, and second positive peaks.

10. The method of claim 9, wherein the first negative peaks comprise local minima in the buffered portion of the raw signal and the second negative peaks comprise local minima in the filtered raw signal, the first positive peaks comprise local maxima in the buffered portion of the raw signal and the second positive peaks comprise local maxima in the filtered raw signal, the first negative going zero crossings comprise transitions in the buffered portion of the raw signal from the first positive peaks to the first negative peaks and the second negative going zero crossings comprise transitions in the filtered raw signal from the second positive peaks to the second negative peaks, and the first positive going zero crossings comprise transitions in the buffered portion of the raw signal from the first negative peaks to the first positive peaks and the second positive going zero crossings comprise transitions in the filtered raw signal from the second negative peaks to the second positive peaks.

11. The method of claim 9, wherein the first correction factor is associated with a timing difference between corresponding second negative peaks in the filtered raw signal and the first negative peaks in the buffered portion of the raw signal, and the second correction factor is associated with a timing difference between corresponding second positive zero-crossings in the filtered raw signal and the first positive zero-crossings in the buffered portion of the raw signal.

12. The method of claim 9, wherein:
determining the timing of slow wave events in the buffered portion of the raw signal comprises aligning and averaging segments of the buffered portion of the raw signal around the first negative peaks in the buffered portion of the raw signal; and
determining the timing of slow wave events in the filtered raw signal comprises aligning and averaging segments of the filtered raw signal around the second negative peaks in the filtered raw signal.

13. The method of claim 12, wherein averaging comprises time lock averaging, event lock averaging, or negative peak lock averaging.

14. The method of claim 8, wherein the output signals comprise an electroencephalogram (EEG) output signal, and the information in the output signals comprises slow waves and/or k-complexes.

15. A system for adjusting timing of stimulation provided to a subject during a sleep session, the system comprising:
means for providing stimulation to the subject;
means for generating output signals conveying information related to brain activity of the subject during the sleep session, the brain activity comprising slow wave activity in the subject during the sleep session;
means for receiving a raw signal from the means for generating output signal;
means for buffering a portion of the raw signal, the buffered portion having one or more buffered portion characteristics;
means for determining a timing of slow wave events in the buffered portion of the raw signal, the timing of the slow wave events determined based on the one or more buffered portion characteristics of the buffered portion of the raw signal;
means for filtering the raw signal to reduce noise artifacts and distortions in the raw signal, the filtered raw signal having one or more filtered raw signal characteristics;
means for determining a timing of slow wave events in the filtered raw signal based on the one or more filtered raw signal characteristics of the filtered raw signal, the slow wave events in the filtered raw signal corresponding to the slow wave events in the buffered portion of the raw signal;
means for comparing the timing of the slow wave events in the buffered portion of the raw signal to the timing of the slow wave events in the filtered raw signal;
based on the comparison, means for determining a first correction factor associated with reducing slow wave activity in the subject and/or a second correction factor associated with enhancing slow wave activity in the subject; and
means for controlling the means for providing stimulation to adjust a timing of the stimulation provided to the subject during the sleep session based on the first correction factor to reduce slow wave sleep in the subject, and/or based on the second correction factor to enhance slow wave sleep in the subject.

16. The system of claim 15, wherein the one or more buffered portion characteristics of the buffered portion of the raw signal comprise first negative going zero crossings, first negative peaks, first positive going zero crossings, and first positive peaks, and the one or more filtered raw signal characteristics comprise second negative going zero crossings, second negative peaks, second positive going zero crossings, and second positive peaks.

17. The system of claim 16, wherein the first negative peaks comprise local minima in the buffered portion of the raw signal and the second negative peaks comprise local minima in the filtered raw signal, the first positive peaks comprise local maxima in the buffered portion of the raw signal and the second positive peaks comprise local maxima in the filtered raw signal, the first negative going zero crossings comprise transitions in the buffered portion of the raw signal from the first positive peaks to the first negative peaks and the second negative going zero crossings comprise transitions in the filtered raw signal from the second positive peaks to the second negative peaks, and the first positive going zero crossings comprise transitions in the buffered portion of the raw signal from the first negative peaks to the first positive peaks and the second positive going zero crossings comprise transitions in the filtered raw signal from the second negative peaks to the second positive peaks.

18. The system of claim 16, wherein the first correction factor is associated with a timing difference between corresponding second negative peaks in the filtered raw signal and the first negative peaks buffered portion of the raw signal, and the second correction factor is associated with a timing difference between corresponding first positive zero-crossings in the filtered raw signal and the second positive zero-crossings in the buffered portion of the raw signal.

19. The system of claim 16, wherein:
   determining the timing of slow wave events in the buffered portion of the raw signal comprises aligning and averaging segments of the buffered portion of the raw signal around the first negative peaks in the buffered portion of the raw signal; and
   determining the timing of slow wave events in the filtered raw signal comprises aligning and averaging segments of the filtered raw signal around the second negative peaks in the filtered raw signal.

20. The system of claim 19, wherein averaging comprises time lock averaging, event lock averaging, or negative peak lock averaging.

21. The system of claim 15, wherein the means for generating output signals are configured such that the output signals comprise an electroencephalogram (EEG) output signal, and the information in the output signals comprises slow waves and/or k-complexes.

* * * * *